United States Patent
Schildkraut et al.

(10) Patent No.: US 7,453,983 B2
(45) Date of Patent: *Nov. 18, 2008

(54) RADIATION THERAPY METHOD WITH TARGET DETECTION

(75) Inventors: Jay S. Schildkraut, Rochester, NY (US); Nathan D. Cahill, West Henrietta, NY (US); Sreeram Dhurjaty, Rochester, NY (US); Lawrence A. Ray, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 326 days.

This patent is subject to a terminal disclaimer.

(21) Appl. No.: 11/039,422

(22) Filed: Jan. 20, 2005

(65) Prior Publication Data

US 2006/0182326 A1     Aug. 17, 2006

(51) Int. Cl.
*A61N 5/10* (2006.01)
*A61B 6/00* (2006.01)
(52) U.S. Cl. .................................. 378/65; 378/205
(58) Field of Classification Search .................. 378/65, 378/205
See application file for complete search history.

(56) References Cited

U.S. PATENT DOCUMENTS

| | | | |
|---|---|---|---|
| 4,996,413 A | 2/1991 | McDaniel et al. | |
| 5,207,223 A * | 5/1993 | Adler | 600/427 |
| 5,313,066 A | 5/1994 | Lee et al. | |
| 5,956,083 A | 9/1999 | Taylor et al. | |
| 6,307,914 B1 * | 10/2001 | Kunieda et al. | 378/65 |
| 6,385,288 B1 * | 5/2002 | Kanematsu | 378/65 |
| 6,501,981 B1 | 12/2002 | Schweikard et al. | |
| 6,516,046 B1 * | 2/2003 | Frohlich et al. | 378/65 |
| 6,683,934 B1 | 1/2004 | Zhao et al. | |
| 6,842,502 B2 * | 1/2005 | Jaffray et al. | 378/65 |
| 6,914,959 B2 * | 7/2005 | Bailey et al. | 378/65 |
| 2003/0031296 A1 | 2/2003 | Hoheisel | |
| 2004/0158146 A1 | 8/2004 | Mate et al. | |
| 2005/0201516 A1 * | 9/2005 | Ruchala et al. | 378/65 |
| 2005/0251029 A1 * | 11/2005 | Khamene et al. | 600/427 |
| 2007/0053491 A1 * | 3/2007 | Schildkraut et al. | 378/65 |

OTHER PUBLICATIONS

"The Visual Hull Concept for Silhoutte-Based Image Understanding", IEEE Trans. Pattern Analysis and Machine Intellegence, vol. 16, No. 2, pp. 150-162, Feb. (1994).

George W. Sherouse et al., "Computation of Digitally Reconstructed Radiographs For Use In Radiotherapy Treatment Design", Technical Innovations and Notes, Radiation Biol. Phys., vol. 18, pp. 651-658 (1990).

(Continued)

*Primary Examiner*—Edward J Glick
*Assistant Examiner*—Thomas R Artman

(57) ABSTRACT

A method for delivering radiation therapy to a patient using a three-dimensional planning image for radiation therapy of the patient wherein the planning image includes a radiation therapy target. The method includes the steps of: determining desired image capture conditions for the capture of at least one two-dimensional radiographic image of the radiation therapy target using the three-dimensional planning image; detecting a position of the radiation therapy target in the at least one captured two-dimensional radiographic image; and determining a delivery of the radiation therapy in response to the radiation therapy target's detected position in the at least one captured two-dimensional radiographic image.

21 Claims, 4 Drawing Sheets

OTHER PUBLICATIONS

E.C. Ford et al., "Cone-beam CT with megavoltage beams and an amorphous silicon electronic portal imaging device: Potential for verification of radiotherapy of lung cancer", Med. Phys. 29, (12), Dec. (2002), pp. 2913-2924.

Shinichi Shimizu et al., "Detection of Lung Tumor Movement in Real-Time Tumor-Tracking Radiotherapy", Int. J. Radiation Oncology Biol. Phys., vol. 5, No. 2, pp. 304-310, (2001).

Fang-Fang Yin et al., "MR Image-Guided Portal Verification For Brain Treatment Field", Int. J. Radiation Onclogy Biol. Phys., vol. 40, No. 3, pp. 703-711, (1998).

Daniel B. Russakoff et al., "Fast calculation of digitally reconstructed radiographs using light fields", Medical Imaging, SPIE, vol. 5032 (2003), pp. 684-695.

* cited by examiner

RADIATION THERAPY METHOD WITH TARGET DETECTION

FIELD OF THE INVENTION

The invention relates generally to radiation therapy systems, and in particular, to systems that deliver therapeutic radiation based on target detection.

BACKGROUND OF THE INVENTION

This invention provides a method for adaptive radiation therapy (ART) in which the location of target tissue is detected in a digital radiograph in order to insure proper targeting of therapeutic radiation.

Many improvements in radiation therapy have the purpose of delivering therapeutic radiation to a target (such as a cancerous tumor) while minimizing exposure to normal tissue. These improvements allow a greater dose of radiation to be applied to the tumor with the constraint that the dose received by surrounding normal tissue must be limited.

Planning for radiation therapy starts with obtaining a three-dimensional image of the patient while the patient has two or more external markers attached. The imaging modality allows the physician to precisely identify the boundaries of the tumor. Computed tomography (CT), magnetic resonance imaging (MRI), positron emission tomography (PET), and ultrasound can be used for this purpose.

The volume of the tumor as it appears in the image is generally referred to as the gross tumor volume (GTV). The GTV is expanded to take into account microscopic extensions of the tumor. This expanded volume is typically referred to as the clinical tumor volume (CTV). The CTV can be further expanded because of potential setup error in the treatment phase. In the case of extra-cranial tumors, there is also uncertainty in tumor position relative to the external markers due to organ motion. For example, lung tumors move as the patient respires. The expansion of the CTV to compensate for setup error and uncertainties due to organ motion is often referred to as the planned treatment volume (PTV).

During setup for radiation therapy, the patient is positioned so that the PTV is located at the system's isocenter. In order to correctly position the patient, the system detects the position of the external markers. Since the position of the PTV is know relative to these external markers, the system can move the patient into the proper position.

In intensity modulated radiation therapy (IMRT), the therapeutic beam sweeps out an arc about the isocenter so that the PTV receives radiation for the duration of the treatment while other tissue is irradiated for a fraction of the time. As the beam moves, its shape is periodically adjusted by means of a multileaf collimator (MLC) to conform to the shape of the PTV from the perspective of the therapeutic radiation beam. In order to further spare normal tissue, the full dose is given over a number of fractionated treatments. Fractionated treatments usually comprise 20 to 40 partial doses given over a period of several days to several weeks.

The PTV is larger than the CTV because of uncertainty in the location of the target relative to the isocenter that needs to receive the full dose of therapeutic radiation. One source of uncertainty is that the tumor may move relative to the external markers between the time of imaging in the planning phase and setup in the therapeutic phase. Furthermore, since the dose is usually given in fractionated treatments the position of the target may vary relative to the external markers, internal organs, and the isocenter differently at each treatment.

A number of methods have been developed to reduce the uncertainty in the location of the target with respect to the system's isocenter. For example, if organ motion due to respiration is a cause of uncertainty, then it can be reduced by capturing the planning images and performing treatment in a specific respiratory state such as relaxed expiration.

Radiation therapy systems are sometimes equipped with two digital radiography units to obtain stereoscopic x-ray images prior to treatment. These images are compared with digitally reconstructed radiographs (DRR) from the CT images captured in the planning phase. Registration of bone or implanted metal markers in the radiographs and DRRs is used to adjust the position of the patient so that the PTV is at the isocenter.

Electronic portal imaging can be used to confirm the location of the target. In electronic portal imaging, the therapeutic beam is imaged after it passes through the patient. This image can be acquired during radiation therapy or prior to therapy with the therapeutic beam source set to low intensity. A drawback of this method is that therapeutic radiation is generally above 1 MV in photon energy, and consequently has low soft tissue contrast. Also, portal imaging is limited to a single radiation source which can only locate the target in two dimensions at an instance in time. This limitation can be overcome by using collecting portal images at several angles and performing volumetric reconstruction as described by E. C. Ford et al. in "Cone-Beam CT with Megavoltage beams and an amorphous silicon electronic portal imaging device: Potential for Verification of Radiotherapy of Lung Cancer," Med. Phys., Vol. 29, No. 12, pp. 2913-2924 (2002). However, a disadvantage of this method is that target position verification results in significant radiation dose to the patient. Also, with current technology, the time required to verify the target's position is too long to ensure that the target has not moved in the time taken to verify its position.

US Patent Application No. 2004/0158146 (Mate) is directed to a guided radiation therapy system having implanted markers that are excitable by an external radiation source. The implanted markers are imaged so that their position relative to the target is known. During patient setup for radiation treatment, the position of the internal markers are located by a sensor array external to the body. Based on the position of the internal markers as determined by the sensor array, the patient is positioned so that the target is at the isocenter.

U.S. Pat. No. 6,501,981 B1 (Schweilkard) is directed to a method to track an internal target in the presence of respiratory motion. Internal markers are placed near the target. Before treatment, the position of the internal and external markers is imaged as the patient breaths. Based on this image data, a correlation between the position of the internal and external markers is calculated. When the patient is treated, the position of the target is predicted by continuously monitoring the position of the external markers. Periodically, the internal markers are imaged in order to obtain their actual location.

Shinichi et al. in "Detection of Lung Tumor Movement in Real-Time Tumor-Tracking Radiotherapy," Int. J. Radiation Oncology Biol. Phys., Vol. 51, No. 2, pp 304-310 (2001) describes a system for real-time tracking of internal 2.0 millimeter gold markers in three dimensions. Four sets or diagnostic fluoroscopes were used to image the markers. During therapy the target was only irradiated when the marker was detected within a permitted dislocation from a nominal location.

A shortcoming of current methods of radiation therapy is that the clinical tumor volume (CTV) is expanded to include surrounding space in order to compensate for uncertainty in location of the target relative to the isocenter. As a result, normal tissue receives a damaging dose of radiation.

Methods have been developed that use implanted internal markers that reduce target location uncertainty. Unfortunately, marker implantation requires addition surgery and may not be an option if the tumor location is inaccessible or if too many tumors are present. Also, the position of an internal marker may not be perfectly correlated with the position of the target.

A feature of the present invention is to provide a system in which the location of the target can be determined accurately. Another feature of the present invention is to provide a system that does not employ internal markers for target location. Another feature of the present invention is to provide a system in which the location of the target can be determined quickly and without significant additional radiation exposure to normal tissue.

SUMMARY OF THE INVENTION

The present invention provides a means to determine the position of the target immediately before irradiation with the therapeutic beam.

More particularly, in the planning phase, an image of the patient is captured using a three-dimensional medical imaging modality. A doctor delineates the boundary of the target in this image.

One or more optimal digitally reconstructed radiographs (DRR) are produced from the planning image. A DRR is optimal when detectability of target tissue is facilitated. In general, overlap of the target tissue with other anatomical structures should be minimized. Also, the boundary of the target in the DRR should be distinct.

The radiation therapy system is equipped with one or more adjustable digital radiographic units. Each digital radiographic unit is arranged to produce a radiograph from the perspective of an optimal DRR.

Immediately before application of the therapeutic beam one or more digital radiographs are captured. An image-processing unit identifies the position of the target in the radiographs based on characteristics of the target in the planning image.

The output of the image-processing unit is used in a variety of ways. If the target is not at the isocenter the system reframes from irradiation with a therapeutic beam. Alternatively, either the patients or the beam is repositioned so that the target is at the isocenter before radiotherapy begins.

According to one aspect of the present invention, there is provided a method for delivering radiation therapy to a patient using a three-dimensional planning image for radiation therapy of the patient wherein the planning image includes a radiation therapy target. The method includes the steps of: determining desired image capture conditions for the capture of at least one two-dimensional radiographic image of the radiation therapy target using the three-dimensional planning image; detecting a position of the radiation therapy target in the at least one captured two-dimensional radiographic image; and determining a delivery of the radiation therapy in response to the radiation therapy target's detected position in the at least one captured two-dimensional radiographic image.

According to another aspect of the present invention, there is provided a method for delivering radiation therapy to a patient using a three-dimensional planning image for radiation therapy of the patient wherein the planning image includes a radiation therapy target. The method includes the steps of: determining one or more desired digital reconstructed radiographs using the planning image; capturing at least one two-dimensional radiographic image corresponding to each of the one or more desired digital reconstructed radiographs using a digital radiography unit; detecting a position of the radiation therapy target in each of the at least one captured digital two-dimensional radiographic images; and determining a delivery of the radiation therapy in response to the radiation therapy target's detected position in the captured at least one two-dimensional radiographic image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
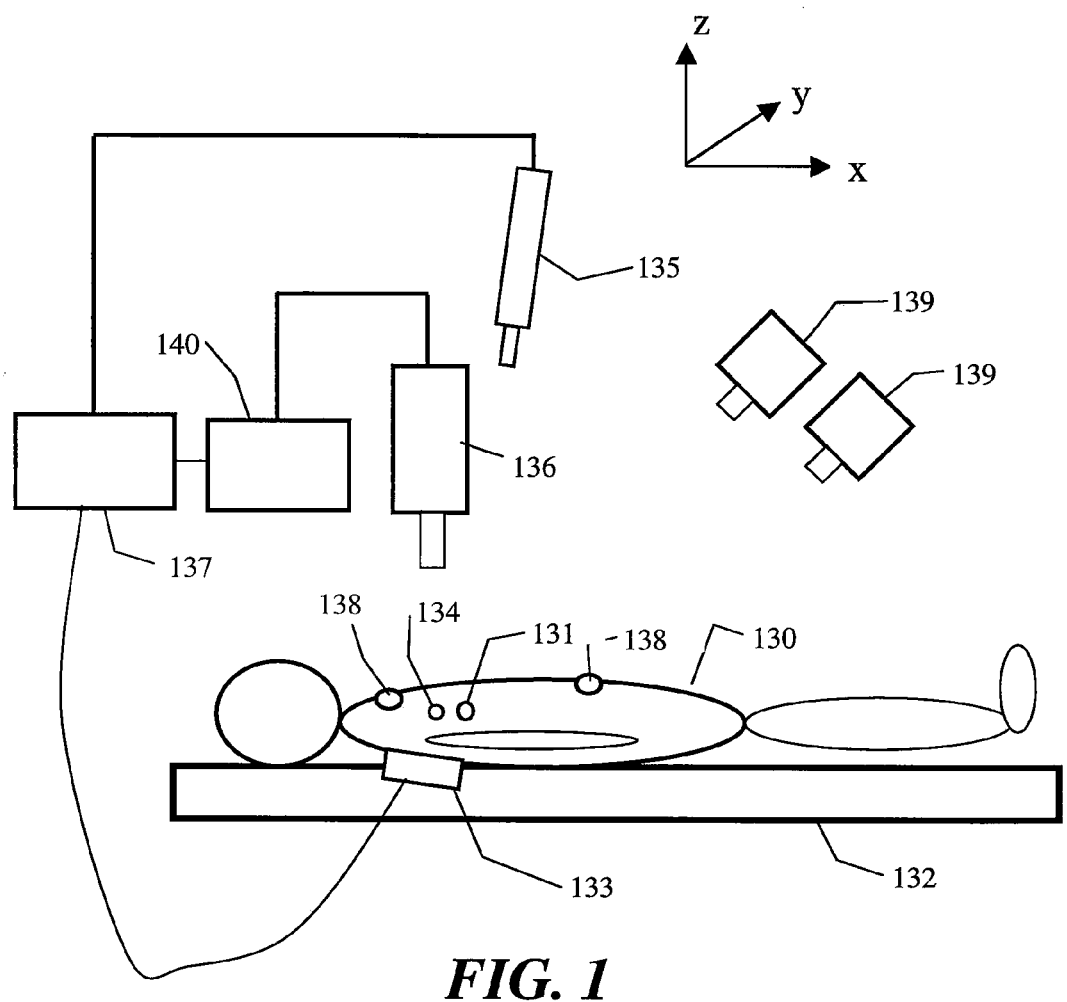
FIG. 1 is a diagrammatic view of the radiation therapy apparatus with target location detection.

The following is a detailed description of the preferred embodiments of the invention, reference being made to the drawings in which the same reference numerals identify the same elements of structure in each of the several figures.

FIG. 1 shows an exemplary radiation therapy system with automatic target location detection. Referring to FIG. 1, the patient 130 is positioned on a support member such as a treatment couch 132. The patient has two or more external markers 138 attached. The position of the external markers is monitored with cameras 139.

A therapeutic radiation source 136 is aimed at the isocenter 134 throughout treatment.

A radiography unit is comprised of a diagnostic x-ray source 135 and digital x-ray imaging device 133 images the region of the target 131. The radiation therapy system preferably has more that one radiography unit to enable the location of the target in three-dimensions.

The diagnostic x-ray source 135 and digital x-ray imaging device 133 have means to accurately determine their position and orientation. This can be accomplished, for example, with the use of markers that are detected by the cameras 139 or by any other means of measuring position and orientation. The relative position and orientation of the diagnostic x-ray source and digital x-ray imaging device is used to determine the magnification and distortion of the target and other anatomy in a radiograph. Furthermore, the location and orientation of the diagnostic x-ray source 135 and digital x-ray imaging device 133 relative to the coordinate system of the therapeutic radiation source 136 and isocenter 134 is also accurately measured. In an embodiment of this invention the cameras 139 detect the location of markers on the diagnostic x-ray source 135 and digital x-ray imaging device 133 and automatically determine their location and orientation relative to the coordinate system of the therapeutic radiation source 136 and isocenter 134.

The target detection and control unit 137 in FIG. 1 provides a variety of functions. It arranges the radiography units to capture images in which the detection of the target is facilitated. It causes the radiography units to capture images immediately before and possibly during treatment. It determines the location of the target in the captured radiographs relative to the radiotherapy coordinate system in which the isocenter is defined. It further provides information to the radiation therapy control unit 140 that can be used in several ways. The information can be used to decide if radiation therapy should commence or not. The information can be used to decide if radiation therapy should continue or be stopped. It can be used to reposition the patient or the therapeutic radiation source so that the target is at the isocenter.

In an embodiment of this invention, during radiation therapy the therapeutic radiation source 136 is imaged either continuously or periodically. The location of the target is detected in these images to verify that it remains at the isocenter. If the target has moved out of position then radiation therapy is terminated.

Figure 2:
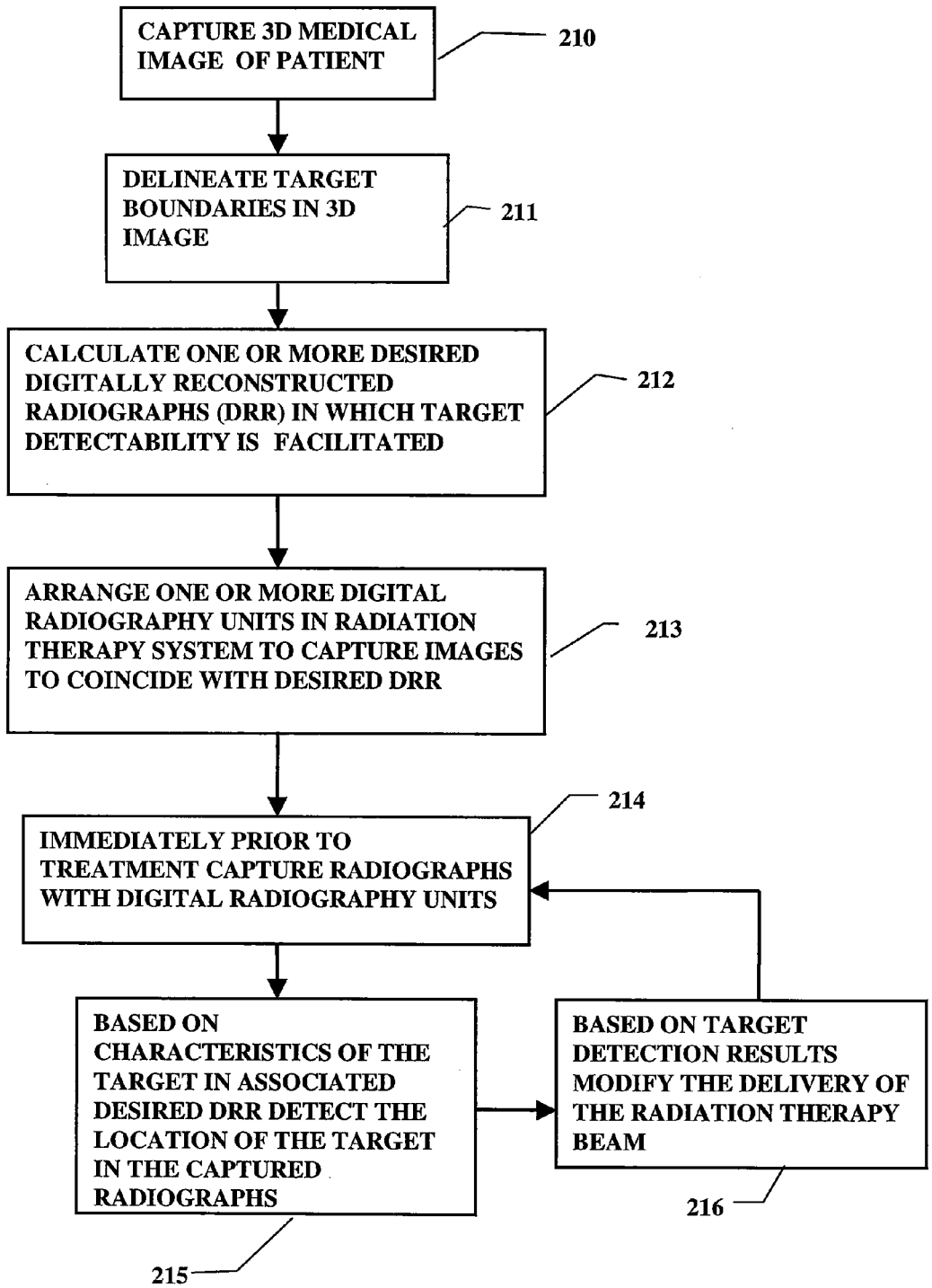
FIG. 2 is a flow chart illustrating the method of the radiation therapy with target location detection in accordance with the present invention.

A method of radiation therapy with target detection in accordance with the present invention is diagrammed in FIG. 2. The process begins with step 210 wherein a planning image is captured of the patient. Medical imaging modalities that can be used for this purpose include computed tomography (CT), magnetic resonance imaging (MRI), positron emission tomography (PET), PET-CT, ultrasound, and the like. In step 211, an operator, possibly with the aid of image segmentation software, delineates the boundary of the target.

The purpose of step 212 is to determine the best capture conditions for digital radiographs that are acquired in step 214. In step 212, digitally reconstructed radiographs (DRR) are calculated from the planning image. The operator or computer software determine one or more DRR for which target detection is facilitated. Generally target detection is facilitated when overlap of normal anatomy with the target is minimized and the boundary of the target is distinct.

In step 213, one or more radiographic units are arranged to capture images that coincide to a DRR as determined in step 212.

Step 214 occurs immediately before patient exposure with the radiation therapy beam. An image is capture with each of the radiographic units as shown in FIG. 1 by the diagnostic x-ray source 135 and digital x-ray detector 133.

In step 215 in FIG. 2, the target is detected in the radiographs captured using the radiographic units. Detection of the target in two or more radiographs enables the localization of the target in three dimensions.

In step 216, the delivery of therapeutic radiation is modified based on the results of step 215. Modification options include, but are not limited to, administering the dose, refraining from administering the dose, repositioning the patient, redirecting the therapeutic radiation beam, and modifying the therapeutic radiation beam. If the modification includes repositioning, redirecting, or modifying, the dose can be administered after the repositioning, redirecting, or modifying.

The diagnostic x-ray source (element 135 shown in FIG. 1) typically includes a transformer to increase the voltage level of the input electrical power and a rectifier to convert the voltage to a single polarity. The x-ray source contains an x-ray tube in which electrons that are ejected from a cathode are accelerated towards an anode target. The collision of electrons with the target results in the production of x-ray photons. The distribution of x-ray energies that reach the patient depends on several factors including the voltage difference between the anode and cathode and the x-ray attenuation properties of filters that are placed between the source and the patient.

In one embodiment of the present invention, dual energy x-ray image capture is employed, such as disclosed in U.S. Pat. No. 6,683,934 (Zhao). For example, a low and high energy x-ray image can be captured in rapid succession. For example, the low energy x-rays may range from 50 to 70 kVP and the high energy x-rays from 110 to 140 kVP. A feature of this method is that the image captured with high energy shows primarily hard tissue such as bone. The low energy image is of both hard and soft tissue. Using known subtraction processing methods (one such method is described in U.S. Pat. No. 6,683,934), an image can be obtained in which hard tissue overlap of soft tissue is removed. This can facilitate the detection of soft tissue targets.

Several types of x-ray imaging devices (element 133 in FIG. 1) may be used to capture an image of the target and surrounding volume. For example, a CCD camera in conjunction with a scintillator that converts x-ray photons to photons of lower energy may be used.

Preferably, the x-ray detector is either an indirect or direct flat panel type. An indirect plat panel detector consists of a scintillator/photodiode/thin film transistor (TFT) structure. Exemplary scintillator materials are Cesium Iodide and Gadolinium Oxysulfide. U.S. Pat. No. 4,996,413 (McDaniel discloses an exemplary indirect x-ray detector suitable for use with the present invention. The photodiode can be crystalline or amorphous silicon. In direct x-ray detectors x-ray photons produce photoelectrons without first being converted to lower energy photons. Direct detectors include an x-ray photoconductor in conjunction with a thin film transistor array. Storage capacitors are also included to collect photo-generated charge. U.S. Pat. No. 5,313,066 (Lee) provides a direct x-ray image-capturing element that can be used in this invention.

The capture of x-ray images that facilitate target detection requires that geometric blur is minimized. Geometric blur decreases with decreasing object to detector distance. During radiation therapy the patient usually lies on a treatment couch (element 132 in FIG. 1). This can cause difficulty in positioning an x-ray imaging device close to a target internal to the patient.

As such, the present invention preferably employs a flexible x-ray imaging device such as the device that is disclosed in U.S. Ser. No. 10/206,730 corresponding to US Patent Application No. 2003/0031296 (Hoheisel). A flexible x-ray imaging device can be build into the treatment couch or placed near the patient with less possibility of damage to the detector.

As previously described, dual energy x-ray image capture facilitates target detection. In one embodiment of the present invention, dual energy capture is accomplished by the use of two or more layers of x-ray imaging elements that are separated by an x-ray filter. For example, the top x-ray imaging element is exposed to the full range of x-ray energy. Below this element is a filter that removes low energy x-ray photons. Next is an x-ray imaging element that is exposed to only high energy x-ray photons. This detector creates a hard tissue image that along with the image from the first detector can be used to produce a difference image in which the detection of soft tissue targets is facilitated.

Methods for calculating DRR (digitally reconstructed radiograph) images are known. For example, a method of calculating DRR (digitally reconstructed radiograph) images from a CT image is provided by G. W. Sherouse, K. Novins, and E. Chaney in "Computation of digitally reconstructed radiographs for use in radiotherapy treatment design," Int. J. Radiat. Oncol. Biol. Phys. 18, 651-658 (1990). In this method, a virtual point source is selected. Ray lines are traced from this source to points in a projection plane. The density at a point in the projection plane is calculated based in the CT number of the voxels in the CT image that are intersected by the ray that extends from the source to that point. In one method the CT number of intersected voxels are converted to linear attenuation coefficients and then summed.

DRR images can also be calculated from an MRI image using the method described by F. F. Yin, et al. in "MR image-guided portal verification for brain treatment field," Int. J. Radiation Oncol. Biol. Phys. 40, 704-711 (1998).

In step 212 in FIG. 2, the target volume boundary from step 211 is used to create one or more DRR that facilitate target detection. This can be accomplished by selecting both the virtual source and projection plane position so that target overlap with other anatomy is minimized and the contrast between the projection of the target volume and surrounding region is maximized. A "target ray" is defined as a ray that passes through the target volume for part of its propagation. Overlap is minimized when target rays pass through regions of low attenuation when outside the target volume. Alternatively, overlap can be effectively minimized when the attenuation of target rays outside of the target volume is uniform. Uniform attenuation can be compensated for so that it does not interfere with target detection. Target rays that intersect the target volume boundary at a small angle define the boundary of the target volume in the projection plane. Contrast is enhanced when the path attenuation of these boundary ray lines differ from adjacent non-target rays.

Another method by which one or more DRR images can be created to facilitate target detection involves selecting both the virtual source and projection plane position so that accounts for the morphological properties of the target volume as accurately as possible. For example, as illustrated in FIG. 4, if the target volume 400 can be closely approximated by an ellipsoid whose major axis is much longer than its minor axis, a DRR whose projection plane is parallel (or whose virtual optical axis is orthogonal) to the major axis enables a more accurate localization of the target volume than a DRR whose projection plane is orthogonal (or whose virtual optical axis is parallel) to the major axis.

Figure 4:
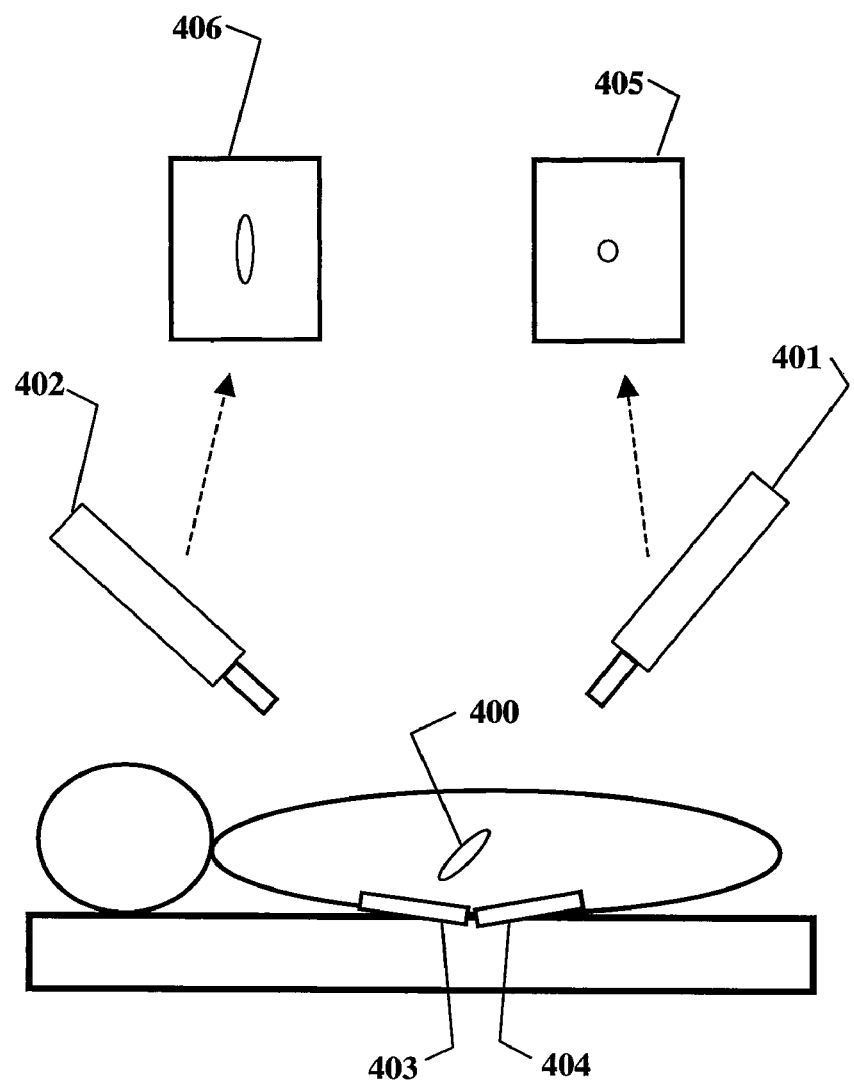
FIG. 4 is a diagrammatic view of the radiation therapy apparatus with target location detection.

This can be illustrated by considering the projection of the target volume 400 as captured with each of the radiographic units as shown in FIG. 4. The first radiographic unit, comprising the diagnostic x-ray source 401 and digital x-ray detector 403, is oriented so that the optical axis is parallel to the major axis of the ellipsoid approximating the target volume 400. The second radiographic unit, comprising the diagnostic x-ray source 402 and digital x-ray detector 404, is oriented so that the optical axis is orthogonal to the major axis of the ellipsoid approximating the target volume 400.

The resulting radiographs 405 (captured by the first radiographic unit) and 406 (captured by the second radiographic unit) illustrate different projections of the target volume 400. The first radiograph 405 shows a projection of the target volume 400 that comprises a much smaller area than the projection of the target volume 400 into the second radiograph 406.

Localization errors in the target volume can be larger along the direction of the optical axes of the radiographic units than along the directions orthogonal to the optical axes; therefore, the localization of the target volume 400 based on the radiograph 405 yields errors that are larger relative to the overall size of the target volume 400 than the localization errors induced by basing localization on radiograph 406.

In more complicated situations (for example, wherein the target volume is not convex), the choice of virtual source and detector plane can be made to optimally locate concavities in the detected target, which further facilitates the construction of a minimal PTV. It is well known in the field of 3-D object modeling that the reconstruction of a target volume from one or more 2-D projections yields a reconstructed volume or "visual hull" that contains only those concavities seen in the projections (see, for example, "The Visual Hull Concept for Silhouette-Based Image Understanding," IEEE Trans. Pattern Analysis and Machine Intelligence, Volume 16, Number 2, pp. 150-162, February 1994). Therefore, a DRR containing a projection of the target volume that illustrates concavities in the target volume enables a more accurate localization of the PTV than a DRR from an arbitrary view.

It is clear to those skilled in the art that the choice of one or more DRR that minimize target overlap with other anatomy and maximize contrast between the projection of the target volume and the surrounding region does not necessarily provide the optimal view of concavities in the target volume; and, conversely, the choice of one or more DRR that provide the best illustration of concavities in the target volume does not necessarily minimize target overlap with other anatomy or maximize contrast between the projection of the target volume and the surrounding region. Therefore, in situations wherein all of (or a majority of) these goals are deemed appropriate, one or more DRR can be created to jointly optimize the goals. This may involve multiple DRR; one or more that are designed to optimize each individual goal, or it may involve one or more DRR that compromise each goal somewhat in order to come up with a better "global" optimum.

The present invention employs the calculation of one or more DRR in order to determine a desired radiograph capture condition that facilitates target detection. In an embodiment of the present invention, light fields are used to increase the speed of DRR calculation as described in "Fast calculation of digitally reconstructed radiographs using light fields," Medical Imaging 2003; Image Processing, Proceedings of SPIE Vol. 5032 (2003), pp. 684-695.

Figure 3:
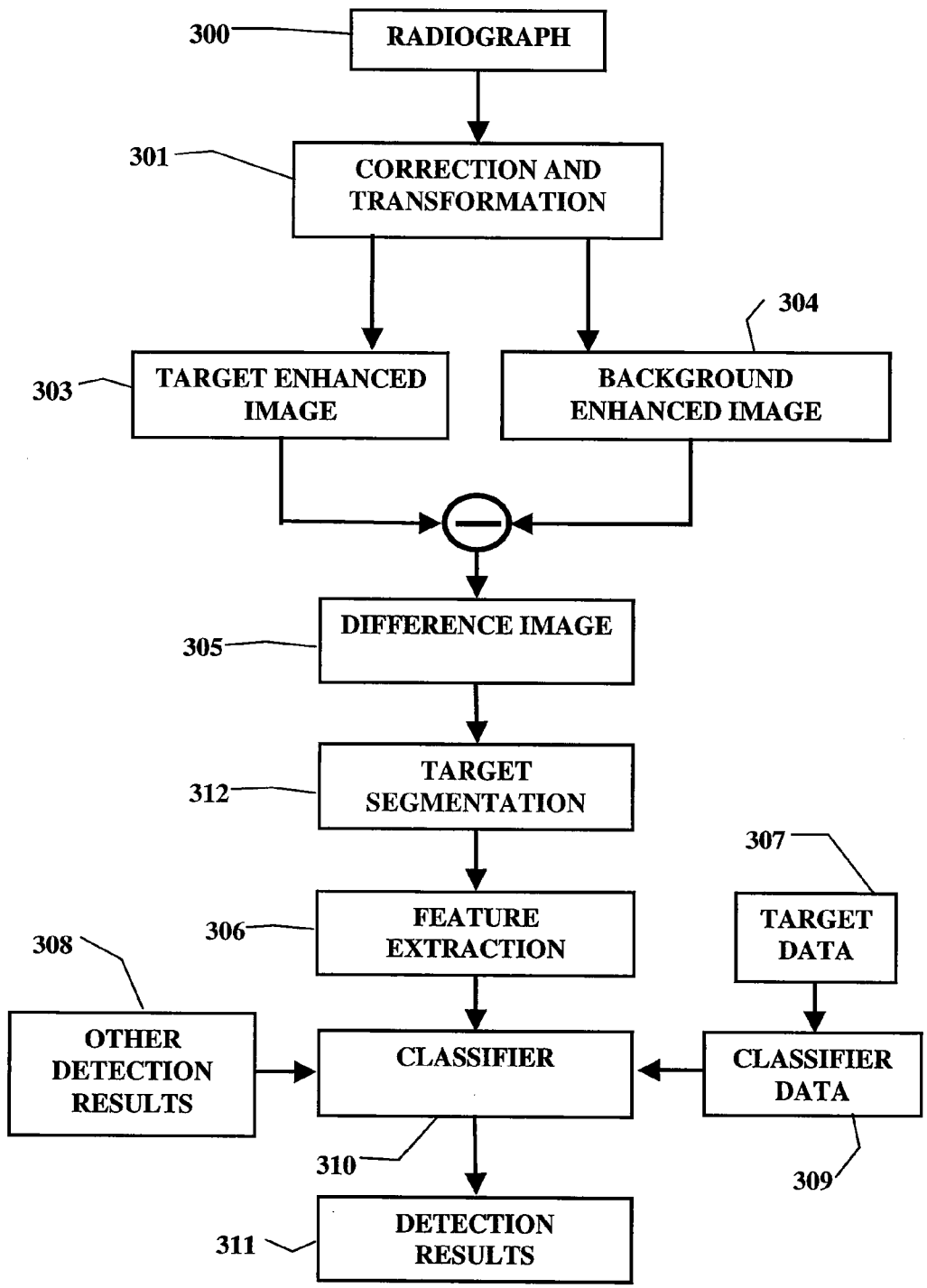
FIG. 3 is a flow chart illustrating the target location method in accordance with the present invention.

In step 215 in FIG. 2 the target is detected in the captured radiographs from step 214 based on characteristics of the target in the DRR computed in step 212. FIG. 3 diagrams the detection process in detail. Referring to FIG. 3, the raw pixel code values of digital radiograph 300 are proportional to the log of the total x-ray attenuation from the source to the detector with additional contributions from scattered x-rays. Furthermore, the properties of the detector, often expressed in terms of its detection quantum efficiency, determine the resolution and signal-to-noise of the digital radiograph. The purpose of the correction and transformation processing step 301 is to correct for system artifacts, to decrease noise, and place the image in a standard form required by subsequent processing steps. Image correction includes compensation for non-uniform x-ray illumination, spatial variation in detector response, and path length through the patient. The image code values may be transformed by application of a look-up-table. One objective is to adjust the mean code value and standard deviation of the image to aim values. In addition, the image may be decomposed into sub-bands of varying resolution. The sub-bands are adjusted and recombined.

Step 303 in FIG. 3 produces an image in which the target is enhanced. An alternative, but equivalent approach is to produce an image in which the target is unchanged, but non-target content is decreased. One method of enhancing the image is to apply a normalized cross correlation with a template that has characteristics of the target. In a preferred embodiment, gray-scale morphological operations are performed on the image. For example, a gray-scale morphological opening with a template that has characteristics of the target will substantially leave the target unchanged but decrease other image content.

In step 304 in FIG. 3, the production of a background or "non-target" enhanced image is similar in principle to step 303 except that the purpose is to enhance non-target content such as normal anatomy or to decrease the target relative to other content. For example, if the primary non-target content in the image are bones such as ribs a gray-scale morphological template can be used that has rib-like characteristics.

In the present invention, templates for target and background image content are based on the characteristics of target and background in the DRR images of step 212 in FIG. 2.

In step 305 the target enhance image has the background enhanced image subtracted from it. In this difference image, the target is characterized by high code values whereas background has low code value. This promotes the identification of the target in subsequent steps.

An objective of step 312 in FIG. 3 is to determine the precise location and extent of the target in the image. As a result of step 305, the target region, if present in the image, will have high code values relative to most other image content. It is also possible the non-target regions will also have a high code value. In step 312, an image segmentation algorithm (for example, watershed segmentation) can be applied to the image in order to identify regions that potentially belong to the target.

In step 306 in FIG. 3, features are extracted from all candidate target regions that were identified in step 312. Extracted features include, but are not limited to, size, shape, gradient magnitude and direction, code value statistics, and texture.

The classification step 310 produces a decision, based on a variety of input, as to whether a candidate target region is actually the target. One input to this step are the features extracted for each candidate target region in step 306. Target detection can be performed concurrently in several radiological images that were capture from different points-of-view. Step 308 shows that intermediate or final target detection results from other images are input to the classification step 310. This information can be used to estimate the prior probability in the classification calculation. Classifiers are well known. Classifiers which can be employed in step 310 include, but are not limited to, support vector machines, Gaussian maximum likelihood (GML), learning vector quantizer (LVQ), k-nearest neighbor, and neural networks.

Another input to the classification step 310 is classifier data 309. Classifier data is produced in a training process in which data on target characteristics 307 is used as input. For example, classifier data may consist of features extracted from the target region as it appears in a DRR calculated in step 212 in FIG. 2.

The output of step 310 in FIG. 3 is a decision 311 as to whether the target was detected and providing its precise location and boundary in the image. The location of the target in two or more images is used to determine the location of the target volume in three-dimensional space. However, in one embodiment of the present invention, the location and magnification of the target in a single image can be used to determine the location of the target volume in three-dimensional space.

In one embodiment of the present invention, instead of detecting the target to which therapeutic radiation is to be applied, critical anatomy that must be spared from therapeutic radiation exposure is detected. In this embodiment, the system refrains from irradiation with a therapeutic beam when critical anatomy is detected within the volume to be exposed by the therapeutic beam.

All documents, patents, journal articles and other materials cited in the present application are hereby incorporated by reference.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for delivering radiation therapy to a patient using a three-dimensional planning image for radiation therapy of the patient wherein the planning image includes a radiation therapy target, the method comprising the steps of:
determining desired image capture conditions for the capture of at least one two-dimensional radiographic image of the radiation therapy target using the three-dimensional planning image;
using the determined image capture conditions to capture the at least one two-dimensional radiographic image;
detecting a position of the radiation therapy target in the captured at least one two-dimensional radiographic image;
determining a delivery of the radiation therapy in response to the radiation therapy target's detected position in the at least one captured two-dimensional radiographic image; and
delivering the radiation therapy.

2. The method of claim 1, wherein the delivery is accomplished by one or more of the following: administering the radiation therapy; refraining from administering the radiation therapy; repositioning the patient; redirecting a therapeutic radiation beam; or modifying the therapeutic radiation beam.

3. The method of claim 1, wherein the image capture conditions are determined using a digitally reconstructed radiograph.

4. The method of claim 1, wherein the desired image capture conditions are determined so as to maximize contrast between the radiation therapy target and its surrounding region.

5. The method of claim 1, wherein the at least one two-dimensional radiographic image is acquired using dual energy.

6. The method of claim 1, wherein the desired image capture conditions is calculated using light fields.

7. The method of claim 1, wherein a radiation therapy apparatus delivers the radiation therapy, and a digital radiography unit is employed to capture the two-dimensional radiographic image, and a position and orientation of the digital radiography unit is determined automatically in a coordinate system of the radiation therapy apparatus.

8. The method of claim 1, further comprising the step of enhancing the radiation therapy target in the at least one two-dimensional radiographic image.

9. The method of claim 1, further comprising the step of enhancing a background anatomy in the at least one two-dimensional radiographic image.

10. The method of claim 1, wherein the position of the radiation therapy target is detected in one of the captured two-dimensional radiographic images based on the detection of the radiation therapy target in another captured two-dimensional radiographic image.

11. The method of claim 1, wherein a position of the radiation therapy target is detected in three-dimensional space using two or more two-dimensional radiographic images.

12. The method of claim 1, wherein a position of the radiation therapy target is detected in three-dimensional space using a location of the radiation therapy target in one two-dimensional radiographic image and the radiation therapy target's magnification.

13. A method for delivering radiation therapy to a patient using a three-dimensional planning image for radiation therapy of the patient wherein the planning image includes a radiation therapy target, the method comprising the steps of:
   determining one or more desired digitally reconstructed radiographs using the planning image;
   capturing at least one two-dimensional radiographic image corresponding to each of the one or more desired digitally reconstructed radiographs using a digital radiography unit;
   detecting a position of the radiation therapy target in each of the at least one captured digital two-dimensional radiographic images;
   determining a delivery of the radiation therapy in response to the radiation therapy target's detected position in the captured at least one two-dimensional radiographic image; and
   delivering the radiation therapy.

14. The method of claim 13, wherein a location of the radiation therapy target is detected in the least one two-dimensional radiographic image based on characteristics of the radiation therapy target in at least one of one or more desired digitally reconstructed radiographs.

15. A method for delivering radiation therapy to a patient using a three-dimensional planning image for radiation therapy of the patient wherein the planning image includes a radiation therapy target, the method comprising the steps of:
   determining desired image capture conditions for the capture of at least one two-dimensional radiographic image of the radiation therapy target using the three-dimensional planning image;
   using the determined image capture conditions to capture the at least one two-dimensional radiographic image;
   detecting a position of the radiation therapy target in the captured at least one two-dimensional radiographic image;
   determining a delivery of the radiation therapy in response to the radiation therapy target's detected position in the at least one captured two-dimensional radiographic image; and
   delivering the radiation therapy, and
   wherein the desired image capture conditions are determined so as to minimize an overlap of the radiation therapy target with patient anatomy.

16. A method for delivering radiation therapy to a patient using a three-dimensional planning image for radiation therapy of the patient wherein the planning image includes a radiation therapy target, the method comprising the steps of:
   determining desired image capture conditions for the capture of at least one two-dimensional radiographic image of the radiation therapy target using the three-dimensional planning image;
   using the determined image capture conditions to capture the at least one two-dimensional radiographic image;
   detecting a position of the radiation therapy target in the captured at least one two-dimensional radiographic image;
   determining a delivery of the radiation therapy in response to the radiation therapy target's detected position in the at least one captured two-dimensional radiographic image; and
   delivering the radiation therapy, and
   wherein the desired image capture conditions are determined such that a boundary of the radiation therapy target is distinct.

17. A method for delivering radiation therapy to a patient using a three-dimensional planning image for radiation therapy of the patient wherein the planning image includes a radiation therapy target, the method comprising the steps of:
   determining desired image capture conditions for the capture of at least one two-dimensional radiographic image of the radiation therapy target using the three-dimensional planning image;
   using the determined image capture conditions to capture the at least one two-dimensional radiographic image;
   detecting a position of the radiation therapy target in the captured at least one two-dimensional radiographic image;
   determining a delivery of the radiation therapy in response to the radiation therapy target's detected position in the at least one captured two-dimensional radiographic image; and
   delivering the radiation therapy, and
   wherein the desired image capture conditions are determined such that a portion of the patient's anatomy that overlaps with the radiation therapy target has a substantially uniform attenuation.

18. A method for delivering radiation therapy to a patient using a three-dimensional planning image for radiation therapy of the patient wherein the planning image includes a radiation therapy target, the method comprising the steps of:
   determining desired image capture conditions for the capture of at least one two-dimensional radiographic image of the radiation therapy target using the three-dimensional planning image;
   using the determined image capture conditions to capture the at least one two-dimensional radiographic image;
   detecting a position of the radiation therapy target in the captured at least one two-dimensional radiographic image;
   determining a delivery of the radiation therapy in response to the radiation therapy target's detected position in the at least one captured two-dimensional radiographic image; and
   delivering the radiation therapy, and
   wherein the desired image capture conditions are determined such that a maximum dimension of the radiation therapy target is projected.

19. A method for delivering radiation therapy to a patient using a three-dimensional planning image for radiation therapy of the patient wherein the planning image includes a radiation therapy target, the method comprising the steps of:
   determining desired image capture conditions for the capture of at least one two-dimensional radiographic image of the radiation therapy target using the three-dimensional planning image;
   using the determined image capture conditions to capture the at least one two-dimensional radiographic image;
   detecting a position of the radiation therapy target in the captured at least one two-dimensional radiographic image;
   determining a delivery of the radiation therapy in response to the radiation therapy target's detected position in the at least one captured two-dimensional radiographic image; and
   delivering the radiation therapy, and
   wherein the desired image capture conditions are determined such that a concavity of the radiation therapy target is obtained.

20. A method for delivering radiation therapy to a patient using a three-dimensional planning image for radiation therapy of the patient wherein the planning image includes a radiation therapy target, the method comprising the steps of:

determining desired image capture conditions for the capture of at least one two-dimensional radiographic image of the radiation therapy target using the three-dimensional planning image;

detecting a position of the radiation therapy target in the captured at least one two-dimensional radiographic image;

determining a delivery of the radiation therapy in response to the radiation therapy target's detected position in the at least one captured two-dimensional radiographic image;

enhancing the radiation therapy target in the at least one two-dimensional radiographic image to generate an enhanced target image;

enhancing a background anatomy in the at least one two-dimensional radiographic image to generate an enhanced background anatomy image; and generating a difference image using the enhanced target image and the enhanced background anatomy image.

21. An apparatus for delivering radiation therapy to a patient using a thee-dimensional planning image for radiation therapy of the patient wherein the planning image includes a radiation therapy target, comprising:

means for determining desired image capture conditions for the capture of at least one two-dimensional radiographic image of the radiation therapy target using the three-dimensional planning image;

means for using the determined image capture conditions to capture the at least one two-dimensional radiographic image;

means for detecting a position of the radiation therapy target in the captured at least one two-dimensional radiographic image;

means for determining a delivery of the radiation therapy in response to the radiation therapy target's detected position in the at least one captured two-dimensional radiographic image; and means for delivering the radiation therapy.

* * * * *